US005143909A

United States Patent [19]

Weintraub et al.

[11] Patent Number: 5,143,909

[45] Date of Patent: Sep. 1, 1992

[54] AMINOSTEROIDS IN A METHOD FOR INHIBITING C17-20 LYASE

[75] Inventors: Philip M. Weintraub, Cincinnati; Cynthia A. Gates, Fairfield; Thomas R. Blohm, Madeira, all of Ohio

[73] Assignee: Merrell Dow Pharmaceuticals Inc., Cincinnati, Ohio

[21] Appl. No.: 671,555

[22] Filed: Mar. 19, 1991

[51] Int. Cl.[5] ........................ A61K 31/56; C07J 41/00

[52] U.S. Cl. ..................................... 514/177; 552/515

[58] Field of Search ......................... 552/515; 514/177

[56] References Cited

U.S. PATENT DOCUMENTS 4,822,528 4/1989 Colombo et al. .................. 552/515

FOREIGN PATENT DOCUMENTS 0291290 5/1987 European Pat. Off. ........... 552/515

OTHER PUBLICATIONS

Johnston, J. O. et al., *Endocrinology*, 115, 776 (1984).

*Primary Examiner*—Howard T. Mars
*Assistant Examiner*—Kimberly J. Kestler
*Attorney, Agent, or Firm*—John J. Kolano

[57] ABSTRACT

The present invention relates to a method for the inhibition of $C_{17-20}$ lyase enzyme which comprises administering to a patient in need of such inhibition, an effective amount of certain 4-amino-17-(hydroxyalkyl or dihydroxyalkyl)steroids or their esters or ethers. Certain of the aminosteroids used in the process are novel compounds.

9 Claims, No Drawings

AMINOSTEROIDS IN A METHOD FOR INHIBITING C17-20 LYASE

BACKGROUND OF THE INVENTION

The enzyme $C_{17-20}$ lyase cleaves the 17-20 carbon-carbon bond in steroids having a carbon substituent at the 17β-position and serves to convert such steroids into the precursors of testosterone, 5α-dihydrotesterone and estrogens. Compounds which inhibit this enzyme would thus serve to inhibit formation of the indicated precursors and would thus be useful in the treatment of various androgen and estrogen dependent disorders. Such treatments would not be limited by the origin of the precursor. Thus, for example the formation of androgens in the adrenal glands would also be inhibited, which is ordinarily not true with regard to other treatments. More specifically, such enzyme inhibitors would be useful in the treatment of prostatic carcinoma, prostatic hyperplasia, virilism, congenital adrenal hyperplasia due to 21-hydroxylase deficiency, hirsutism and estrogen dependent breast tumors. Thus, for example, it is well established that reduction of serum testosterone levels is useful in the treatment of many cases of prostatic carcinoma. In clinical practice, this has been accomplished by orchiectomy or by diethylstilbestrol treatment but the first approach is often psychologically unacceptable while a number of side effects are associated with the second approach. Thus, an alternative approach to testosterone reduction is desirable and this can be accomplished by the administration of compounds which are lyase inhibitors. To the extent that prostatic carcinoma is androgen-dependent and breast tumors are estrogen-dependent, such inhibitors would block the indicated source of androgens or estrogens and thus provide an appropriate treatment for the indicated condition.

DETAILED DESCRIPTION OF THE INVENTION

The present invention relates to a method for the inhibition of $C_{17-20}$ lyase enzyme which comprises administering, to a patient in need of such inhibition, an effective amount of certain 4-amino-17β-(hydroxyalkyl) and 4-amino-17β-(di-hydroxyalkyl) steroids and related compounds wherein the hydroxy group or groups are esterified or etherified. Another aspect of the present invention are those 17-substituted steroids which are used in the method of this invention and which are novel compounds. More particularly, the present invention relates to a method for inhibiting $C_{17-20}$ lyase enzyme which comprises administering to a patient in need of such inhibition, an effective amount of a compound of the formula:

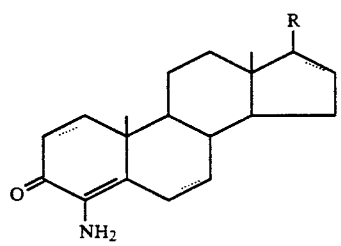

wherein the dotted lines indicate the optional presence of a double bond, R is —($C_{1-6}$ alkyl)—OZ or —($C_{2-6}$ alkyl)-$(OZ)_2$ and Z is hydrogen, $C_{1-6}$ alkyl, phenyl—($C_{1-4}$ alkyl), (Y-substituted phenyl)—($C_{1-4}$ alkyl), $C_{1-6}$ alkanoyl, benzoyl or Y-Substituted benzoyl wherein Y is methyl, halogen or methoxy. The alkyl groups referred to above can be straight- or branched-chain. Examples of such alkyl groups are methyl, ethyl, propyl, isopropyl, butyl, sec-butyl and pentyl. When these alkyl groups are substituted by two —OH groups, the two —OH groups are not located on the same carbon atom. Examples of the halogen substituents referred to above are fluorine, chlorine and bromine. Some specific examples of the two types of OH-substituted alkyl groups referred to above hydroxymethyl, 1-hydroxyethyl, 2-hydroxyethyl, 1,2-dihydroxyethyl, 1-methyl-2-hydroxyethyl, 1-hydroxypropyl and 3-hydroxypropyl. Examples of etherified R-groups (i.e., Z is alkyl or phenylalkyl) are 2-methoxy-1-methylethyl and 2-(phenylmethoxy)-1-methylethyl. Examples of esterified R-groups (i.e., Z is alkanoyl, benzoyl or substituted benzoyl) are 2-acetyloxy-1-methylethyl and 2-benzoyloxy-1-methylethyl. In those cases where optical isomerism is possible in the R-substituent, the individual pure optical isomers are each part of this invention.

The novel compounds of the present invention correspond to the compounds as set forth above with regard to the method but with the proviso that R can not be 1-hydroxyethyl or 1-methyl-2-hydroxyethyl.

Acid addition salts of the aforesaid amino compounds, with pharmaceutically acceptable acids, are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acids.

The activity for the compounds of the present method as inhibitors of steroid $C_{17-20}$ lyase was determined by the following procedure and expressed as the IC5s. Microsomes were isolated from human testis tissue, using testes obtained from therapeutic orchiectomies. The compound to be tested was dissolved in dimethyl sulfoxide and diluted in 0.05M sodium phosphate buffer, pH 7.4, to give the desired concentration of the test compound. The assay mixture also contained 1 mM NADPH, 5 mM glucose-6-phosphate, 1 I.U./ml glucose-6-phosphate dehydrogenase, and 0.64 mg microsomal protein in a total volume of 0.2 ml. Control assays contained all components, including dimethyl sulfoxide, but with no test compound. All assays were performed in duplicate. The reaction was initiated by addition of substrate, [7-$^3$H]-17α-hydroxypregnenolone at a final concentration of 0.3M, 0.2 Ci total activity per assay; the complete assay was incubated at 34° C. for 6 minutes. Each reaction was stopped by the addition of 5 ml of chloroform:methanol, 2:1. Carrier steroids representing substrate and products (dehydroepiandrosterone and androst-5-ene-38,17β-diol) and 0.8 ml of water were added at this time. The steroids were extracted by the method of Moore and Wilson (*Methods in Enzymol.*, eds., B. W. O'Malley and J. G. Hardman, 36, 1975, p. 466–474), the organic phase containing the steroids was evaporated under nitrogen gas and the residues were dissolved in 18% tetrahydrofuran (v/v) in hexane, and the steroids were separated by HPLC on a Si60 (5 μM) column (250×40 mm) using a gradient of 18-22% tetrahydrofuran (v/v) in hexanol. Radioactivity in the steroid peaks was measured by a Radiomatic Model HS Flo-One detector.

The enzyme activity for each incubate was calculated from the percent conversion of substrate to products, and the results were expressed determined as percent inhibition of control. The $IC_{50}$ values were determined by fitting these data to the two parameter equation in the appropriate computer program. Using this procedure, the following results were observed for compounds used in the method of this invention:

| TEST COMPOUND | $IC_{50}$ |
|---|---|
| (20S)-4-Amino-21-hydroxy-20-methylpregn-4-en-3-one | 51 nM |
| (20S)-4-Amino-21-hydroxy-20-methylpregna-4,6-dien-3-one | 119 nM |

The method of inhibition of $C_{17-20}$ lyase according to the present invention can be useful for the treatment of various androgen- or estrogen-dependent disorders. Thus, the present invention would encompass a method for treating androgen- or estrogen-dependent disorders which comprises administering to an individual suffering from such a disorder an effective amount of a compound of the method of the present invention. More particularly, the present method is useful in the treatment of prostatic carcinoma, benign prostatic hyperplasia, virilism, congenital adrenal hyperplasia due to 21-hydroxylase deficiency, hirsutism and estrogen dependent breast tumors. The compounds used in the method of this invention are also active as inhibitors of the enzyme 5α-reductase. Thus, when $C_{17-20}$ lyase is inhibited according to the method of this invention, 5α-reductase can also be inhibited so that a combination of effects can be observed.

In the treatment of benign prostatic hypertrophy (BPH) the compounds of the invention may be administered in various manners to the patient being treated to achieve the desired effect. As used herein in the treatment of BPH, the term patient is taken to mean male warm blooded animals, such as male dogs and human males. The compounds can be administered alone or in combination with one another. Also, the compounds can be administered in the form of a pharmaceutical preparation. The compounds may be administered orally, parenterally, for example, intravenously, intraperitoneally, intramuscularly or subcutaneously, including injection of the active ingredient directly into the prostate. Slow release implants can also be used. The amount of compound administered will vary over a wide range and can be any effective amount. Depending on the patient to be treated, the condition being treated and the mode of administration, the effective amount of compound administered will vary from about 0.001 to 10 mg/kg of body weight per day and preferably from 0.01 to 1.0 mg/kg of body weight per day. Unit dosages for oral or parenteral administration may contain, for example, from 0.2 to 500 mg of a compound of the invention.

These dosage ranges represent the amount of compound that will be effective in reducing the size of the prostate, i.e., the amount of compound effective in treating BPH. The compounds can be administered from onset of hypertrophy of the prostate to regression of the symptoms, and may be used as a preventive measure.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and solutions for injection. The compounds are most preferably administered in oral dosage forms.

The nature of the pharmaceutical composition and the pharmaceutical carrier or diluent will, of course, depend on the desired route of administration, i.e., orally or parenterally. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maize-starch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration, solutions or suspensions of a compound of the present invention with conventional pharmaceutical vehicles may be employed, e.g., as a solution for intravenous injection or as an oily suspension for intramuscular injection. Procedures for the preparation of compositions as discussed above are described in standard texts, such as *Remington's Pharmaceutical Sciences,* Mack Publishing Company, Easton, Pa.

The following are illustrative pharmaceutical formulations suitable for oral administration which may be employed in practicing the present invention:

| TABLET | |
|---|---|
| (a) (20S)-4-amino-21-hydroxy-20-methyl-pregn-4-en-3-one | 75 g |
| (b) Lactose | 1.216 Kg |
| (c) Corn starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| | |
|---|---|
| (a) Magnesium stearate | 0.015 Kg |
| (b) Corn starch qs ad | 1.725 Kg |

Compress on a suitable tablet machine to a weight of 0.115 g/tablet.

| SOFT GELATIN CAPSULE | |
|---|---|
| (a) (20S)-4-amino-21-hydroxy-20-methyl-pregn-4-en-3-one | 0.25 Kg |
| (b) Polysorbate 80 | 0.25 Kg |

-continued

| SOFT GELATIN CAPSULE | |
|---|---|
| (c) Corn oil qs ad | 25.0 Kg |

Mix and fill into 50,000 soft gelatin capsules.

The 4-amino-4-ene compounds referred to above are prepared by the reaction of an azido compound of the structure:

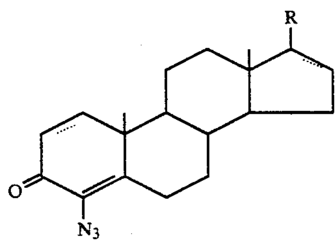

wherein the dotted lines and R are defined as above, with triphenylphosphine with heating in an aqueous inert solvent. Aqueous tetrahydrofuran is an example of a useful solvent for the reaction.

The 4-azidosteroid-4-ene compound used as the starting material above is obtained by reacting the corresponding 4,5-epoxy compound with sodium azide in an inert solvent such as dimethyl sulfoxide in the presence of a catalytic amount of sulfuric acid. The reaction mixture is heated at 60° C. to give the azido compound.

The 4-amino-4,6-diene compounds referred to above are obtained by the reaction of a 4,5-epoxy compound of the formula:

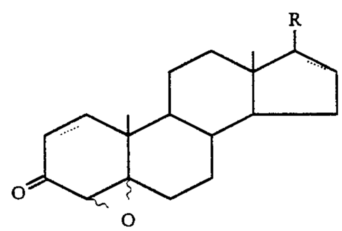

wherein the dotted lines and R are defined as above, with sodium azide in an inert solvent such as dimethyl sulfoxide. The reaction is carried out in the presence of a catalytic amount of a strong acid, such as sulfuric acid, with heating at 100° C. No effort is made to isolate any intermediates but it appears that the epoxide is first opened to give the 4-azido-4-ene. Under the reaction conditions used, the azido compound loses nitrogen, a putative 4-imino-5-ene forms, and this tautomerizes to give the desired 4-amino-4,6-diene. The amino compound obtained in this way can be further reacted with an appropriate anhydride to give the corresponding 4-amido compound. In the case of the formamido compound, mixed formic acetic anhydride, prepared in situ, is used as the anhydride.

The 4,5-epoxy compounds, used as the starting materials above, are themselves obtained by the base catalyzed epoxidation of the appropriate corresponding 4-ene using 30% aqueous hydrogen peroxide. For those compounds containing a double bond at the 1-position, it is more convenient to introduce that unsaturation after the epoxide is formed. Thus, for example, treatment of a 4,5-epoxy 3-ketone with dichlorodicyanoquinone gives the corresponding $\Delta^1$ epoxide compound. The epoxide product obtained is generally a mixture of the $\alpha$ and $\beta$-epoxides with the $\beta$-epoxide being the preponderant product. In some instances, a single isomer is obtained. In any case, further reaction of the epoxides with sodium azide as described earlier gives the desired 4-amino-4,6-diene.

The steroid 4-enes, which are used as the starting materials in the preceding paragraph, are themselves known compounds or they can be prepared by known standard chemical procedures. The starting materials containing an ether group in the 17-substituent can be prepared from the corresponding alcohol. Thus, for example, a 17-(hydroxyalkyl substituted) steroid-4-en-3-one is first converted to the corresponding 3-methoxysteroid-3,5-diene by reaction with trimethyl orthoformate and a trace of p-toluenesulfonic acid in dioxane as the solvent. Pyridine is used to work up this reaction mixture. The resulting alcohol is then reacted with sodium hydride in dimethylformamide to give the corresponding sodium salt which is then reacted with the appropriate halide, such as methyl iodide or benzyl chloride, to give the corresponding compound containing an ether group as part of the 17-substituent. This ether is then treated with 10% hydrochloric acid, either as part of the general isolation procedure or after isolation of the crude product, to convert the 3-enol ether structure back to the desired steroid-4-en-3-one.

The compounds used in the present method can be prepared by the procedures described in the following examples.

EXAMPLE 1

(20S)-4,5-Epoxy-21-hydroxy-20-methylpregnan-3-one

A solution of (20S)-21-hydroxy-20-methylpregn-4-en-3-one (12.8 mmole) in methanol (55 mL) and dichloromethane (11 mL) was cooled to 12° C. and treated in one portion with 30% aqueous hydrogen peroxide (3.3 mL) followed by dropwise addition of an aqueous sodium hydroxide solution prepared by dissolving sodium hydroxide (0.38 g) in water (2.2 mL). After one hour, the cooling bath was removed and the reaction was stirred for an additional 3 hours. Most of the solvent was then removed in vacuo. The residue was dissolved in dichloromethane and purified by flash chromatography (hexane-20% ethyl acetate and hexane-40% ethyl acetate) to give (20S)-4,5-epoxy-21-hydroxy-20-methylpregnan-3-one (73.1%). This material was a mixture of the $4\alpha,5\alpha$- and $4\beta,5\beta$-isomers and it was used as is in further reactions.

EXAMPLE 2

(20S)-4-Azido-21-hydroxy-20-methylpregn-4- -one

A solution of (20S)-4,5-epoxy-21-hydroxy-20-methylpregnan-3-one (9.29 mmole) in dimethyl sulfoxide (50 mL), under a nitrogen atmosphere, was placed into an oil bath heated to 60° C. The solution was stirred vigorously as sodium azide (9.74 g, 149.8 mmole) was slowly added. Concentrated sulfuric acid (0.6 mL) was then added dropwise and the mixture was stirred at 60° C. for 90 minutes. The reaction flask was removed from the oil bath and cooled to room temperature. The resulting solid mass was broken up and poured into ice-cold water (500 mL). The mixture was stirred for 30–45 minutes after which the solids were collected by filtration, washed with water and sucked dry to give crude azide. The azide was taken up in dichloromethane and purified by flash chromatography through a column of silica gel eluting with hexane-15% ethyl acetate and hexane-30% ethyl acetate. Fractions containing the desired product were combined and concentrated in vacuo to give (20S)-4-azido-21-hydroxy-20-methylpregn-4-en-3-one. IR 3408, 2112, 1676 $cm^{-1}$; MS (CI) m/z 372 (5%, M+1), 344 (100%, M+1-$N_2$); (EI) m/z 371 (3%, M), 55 (100%); $^1$H NMR $CDCl_3$) δ 0.70 (3H, s $C_{18}$-Me), 1.04 (d, $C_{21}$-Me), 1.18 (S, $C_{19}$-Me), 2.41–2.60 (2H, m), 3.20 (1H, dq, $C_6$-H), 3.38 (1H, dd, ½ $C_{21}$-$CH_2$), 3.63 (1H, dd, ½ $C_{21}$-$CH_2$); $^{13}$C NMR ($CDCl_3$) δ 128.39, 155.34, 193.26.

EXAMPLE 3

(20S)-4-Amino-21-hydroxy-20-methylpregn-4-en-3-one

To a stirred solution of (20S)-4-azido-21-hydroxy-20-methylpregn-4-en-3-one (3.15 mmole) in tetrahydrofuran (20 mL)-water (7 mL) was added triphenylphosphine (1.41 g, 5.38 mmole). The reaction was heated at reflux temperature for 16 hours. Most of the tetrahydrofuran was removed under vacuum. Dichloromethane was added to the mixture and the organic solution was placed atop a column of silica gel and flash chromatographed (hexane-30% ethyl acetate). The fractions containing the product were combined and concentrated to a white solid which was crystallized from diethyl ether to give (20S)-4-amino-21-hydroxy-20-methylpregn-4-en-3-one. IR 3510, 3470, 3384, 1648, 1614, 1576 $cm^{-1}$; MS (CI) 346 (100%, $M^+$+1) (EI) 345 (65%, $M^+$), 302 (100%); 1H NMR δ ($CDCl_3$) 0.73 (3H, s, $C_{18}$-Me), 1.04 (d, $C_{21}$-Me), 1.15 (s, $C_{19}$-Me), 2.42–2.56 (3H m) 3.73 (v br $NH_2$) 3.36 (1H dd ½ $C_{21}$-$CH_2$), 3.63 (1H, dd, ½ $C_{21}$-$CH_2$); $^{13}$C NMR δ ($CDCl_3$) 132.85, 139.15, 194.38. This compound has the following structure:

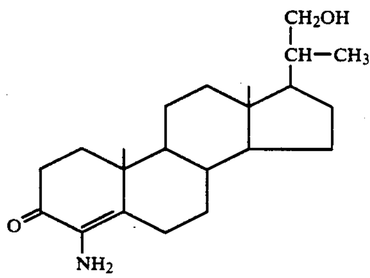

EXAMPLE 4

(20S)-4-Amino-21-hydroxy-20-methylpregna-4,6-dien-3-one

A solution of (20S)-4,5-epoxy-21-hydroxy-20-methylpregnan-3-one (7.7 mmole) in dimethyl sulfoxide (40 mL), under a nitrogen atmosphere, was placed in an oil bath heated at 60° C. The solution was stirred vigorously as sodium azide (8.11 g, 0.338 mole) was slowly added. After the addition of the azide was complete, concentrated sulfuric acid (0.54 mL) was added. The bath temperature was raised to 100° C. and the reaction was stirred at this temperature for 90 minutes. The reaction was removed from the oil bath and cooled to room temperature and the resulting solid mass was broken up and poured into cold water (550 mL). The mixture was stirred for 30 min and the solids were collected by filtration, washed with water and dried to a yellow solid. The crude product was purified by flash chromatography (hexane-30% ethyl acetate) to give (20S)-4-amino-21-hydroxy-20-methylpregna-4,6-dien-3-one. IR 3462, 3390, 3346, 1652, 1616, 1592, 1564 $cm^{-1}$; MS (CI) m/z 344 (100%, $M^+$+1); (EI) m/z 343 (60%, $M^+$), 150 (100%); $^1$H NMR ($CDCl_3$) δ 0.76 (3H, s, $C_{18}$-Me), 1.04+1.05 (6H, s+d, $C_{19}$-Me+$C_{21}$-Me) 2.48 (1H, dq), 2.63 (1H, dq), 3.38 (1H, dd, ½ $C_{21}$-$CH_2$), 3.64(dd+v br, ½ $C_{21}$-$CH_2$+$NH_2$), 5.97 (1H, dd) 6.30 (1H, dd); $^{13}$C NMR ($CDCl_3$) δ 121.77, 132.08, 132.98, 136.55, 194.40.

EXAMPLE 5

(20S)-4,5-Epoxy-21-hydroxy-20-methylpregnan-3-one Acetate

To a solution of (20S)-21-hydroxy-20-methylpregn-4-en-3-one acetate (10.6 g, 28.3 mmole) in methanol (60 mL) and dichloromethane (15 mL) cooled to 15° C. in a cold water bath there was added 30% hydrogen peroxide (6.8 mL) and then, dropwise, a solution of sodium hydroxide (0.49 g) in water (3.2 mL). After 30 minutes, the cold bath was removed and the reaction was stirred for 4 hours at room temperature. The solvents were then removed under reduced pressure and the residue was dissolved in dichloromethane (300 mL) and extracted with brine (100 mL). The organic layer was separated, dried over magnesium sulfate, filtered and concentrated to a solid which was purified by flash chromatography on silica gel to give (20S)-4,5-epoxy-21-hydroxy-20-methylpregnan-3-one acetate (6.1 g, 55.6%) as a mixture of the 4α,5α- and 4,β5β-isomers.

EXAMPLE 6

(20S)-4-Azido-21-hydroxy-20-methylpregn-4-en-3-one Acetate

To a vigorously stirred solution of the (20S)-4,5-epoxy-21-hydroxy-20-methylpregnan-3-one acetate (3.0 g, 7.72 mmole) obtained in the preceding example, in dimethyl sulfoxide (100 mL), there was added sodium azide (8.2 g) and then concentrated sulfuric acid (0.55 mL). The mixture was heated at 60° C. for 1.5 hours and the cooled mixture was poured into cold water (700 mL). After stirring for 30 minutes, the solids were collected by filtration, washed with water and dried by suction. The resulting solid was purified by flash chromatography on silica gel to give (20S)-4-azido-21-hydroxy-20-methylpregn-4-en-3-one acetate as a white solid (1.6 g, 50.1%), melting at 137°–138° C., with decomposition, after recrystallization from aqueous acetone. IR 2120, 1736, 1670, 1588 (m), 1254 $cm^{-1}$; MS (CI) 386 (3%, M+1—$N_2$), 326 (100%, M+1-$N_2$-AcOH); $^1$H NMR ($CDCl_3$) δ 0.72 (3H, s, $C_{18}$-Me), 1.01 (d, $C_{22}$-Me), 1.14 (s, $C_{19}$-Me), 2.06 (s, Ac-Me), 3.02 (1H, dq, $C_6$-H), 3.77 (1H, dd, ½ $C_{21}$-$CH_2$), 4.08 (1H, dd, ½ $C_{21}$-$CH_2$).

EXAMPLE 7

(20S)-4-Amino-21-hydroxy-20-methylpregn-4-en-3-one Acetate

A stirred mixture of (20S)-4-azido-21-hydroxy-20-methylpregn-4-en-3-one acetate (1.4 g, 3.39 mmole), triphenyl-phosphine (1.08 g), tetrahydrofuran (25 mL) and water (7 mL) was heated at reflux temperature under argon for 18 hours. The solvents were removed from the cooled reaction and the residue was purified by flash chromatography to give (20S)-4-amino-21-hydroxy-20-methylpregn-4-en-3-one acetate (1.1 g, 84%). IR 3470, 3366, 1732, 1674, 1618, 1584, 1254 $cm^{-1}$; MS (CI) 388 (100%, M+1), 328 (70% M+1-AcOH); $^1$H NMR ($CDCl_3$) δ 0.72 (3H, s, $C_{18}$-Me), 1.00

(d, $C_{22}$-Me), 1.14 (s, $C_{19}$-Me), 2.04 (s, Ac-Me), 3.43 (2H, v br, $NH_2$), 3.76 (1H, dd, ½ $C_{21}$-$CH_2$), 4.07 (1H, dd, ½ $C_{21}$-$CH_2$). This compound has the following structure:

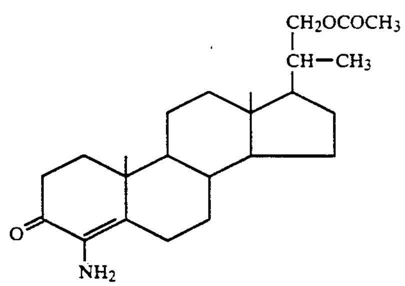

EXAMPLE 8

(20S)-4-Amino-21-hydroxy-20-methylpregna-4,6-dien-3-one Acetate

To a vigorously stirred solution of the (20S)-4,5-epoxy-21-hydroxy-20-methylpregnan-3-one acetate (2.0 g, 5.15 mmole) obtained in Example 6, in dimethyl sulfoxide (70 mL) and heated to 60° C., there was added sodium azide (5.4 g) and then concentrated sulfuric acid (0.37 mL). The mixture was quickly brought to a temperature of 100° C. and held at that temperature for 1 hour. The cooled mixture was then poured into cold water (450 mL). The solids were collected by filtration, washed with water, and dried by suction to give a yellow solid which was purified by flash chromatography to give (20S)-4-amino-21-hydroxy-20-methylpregna-4,6-dien-3-one acetate (1.04 g, 52.5%). IR 3488, 3446, 3360, 1740, 1668, 1612 (m), 1592 (m), 1562 (m), 1252 $cm^{-1}$; MS (CI) 386 (20%, M+1), 326 (100%, M+1-AcOH); $^1H$ NMR ($CDCl_3$) δ 0.78 (3H, s, $C_{18}$-Me), 1.03 (d, $C_{22}$-Me), 1.06 (s, $C_{19}$-Me , 2.07 (s, Ac-Me), 3.69+3.78 (3H, v br+dd, $NH_2$+½ $C_{21}$-$CH_2$ , 4.09 (1H, dd, ½ $C_{21}$-$CH_2$), 5.97 (1H, dd), 6.30 (1H, dd).

EXAMPLE 9

(20S)-21-Hydroxy-20-methylpregn-4-en-3-one Benzoate

A solution of (20S)-21-hydroxy-20-methylpregn-4-en-3-one (8.0 g, 24.2 mmole) in dichloromethane (200 mL) was cooled in an ice-water bath and treated sequentially with triethylamine (3.69 mL, 26.6 mmole) and benzoyl chloride (3.09 mL, 26.6 mmole) and stirred for 16 hours at room temperature. After the reaction mixture was diluted with dichloromethane (200 mL), it was extracted with ether, dried over magnesium sulfate and filtered and the filtrate was concentrated to a solid which was purified by flash chromatography to give (20S)-21-hydroxy-20-methylpregn-4-en-3-one benzoate (9.4 g, 89.5%) melting at 193°-195° C. after recrystallization from acetone. IR 1716, 1676, 1614 (m), 1284 $cm^{-1}$; MS (CI) 435 (100%, M+1), 313 (70%, M+1-PhCOOH); $^1H$ NMR ($CDC_{13}$) δ 0.77 (3H, s, $C_{18}$-Me), 1.04 (d, $C_{22}$-Me), 1.19 (s, $C_{19}$-Me), 4.05 (1H, dd, ½ $C_{21}$-$CH_2$), 4.34 (1H, dd, ½ $C_{21}$-$CH_2$), 5.72 (1H, s, $C_4$-H), 7.45 (2H, t), 7.56 (1H, t), 8.04 (2H, dd).

EXAMPLE 10

(20S)-4,5-Epoxy-21-hydroxy-20-methylprehnan-3-one Benzoate

A solution of (20S)-21-hydroxy-20-methylpregn-4-en-3-one benzoate (8.9 g, 20.5 mmole) in methanol (80 mL) and dichloromethane (80 mL) was cooled to 15° C. and treated sequentially with 30% hydrogen peroxide (5.0 mL) and sodium hydroxide (1.09 g) in water (6.7 mL). After 4 hours at room temperature, the product was isolated from the reaction mixture by the same procedure as described in Example 5 to give (20S)-4,5-epoxy-21-hydroxy-20-methylpregnan-3-one benzoate (1.6 g, 17.3%). IR 1720, 1280 $cm^{-1}$; MS (CI) 451 (95%, M+1), 329 (100%, M+1-PhCOOH); $^1H$ NMR ($CDCl_3$) δ 0.76 (3H, s, $C_{18}$-Me), 1.13 (d, $C_{22}$-Me), 1.16 (s, $C_{19}$-Me), 2.98+3.04 (1H, s+s, $C_4$-H), 4.04 (1H, dd, ½ $C_{21}$-$CH_2$), 4.32 (1H, dd, ½ $C_{21}$-$CH_2$), 7.46 (2H, t), 7.57 (1H, t), 8.04 (1H, dd).

EXAMPLE 11

(20S)-4-Amino-21-hydroxy-20-methylpregna-4,6-dien-3-one Benzoate

To a vigorously stirred solution of (20S)-4,5-epoxy-21-hydroxy-20-methylpregnan-3-one benzoate (1.0 g, 2.22 mmole) in dimethyl sulfoxide (35 mL), heated to 60° C., there was added sodium azide (2.7 g) and the concentrated sulfuric acid (0.2 mL). The mixture was quickly brought to a temperature of 100° C. and held at that temperature for 1 hour. The cooled mixture was then poured onto cold water (250 mL). The resulting mixture was extracted with ether (300 mL) and the ether solution was washed with brine, dried over magnesium sulfate and filtrate and the filtrate was concentrated to give a yellow solid which was purified by chromatography to give (20S)-4-amino-21-hydroxy-20-methylpregna-4,6-dien-3-one benzoate (0.8 g, 80.1%) melting at 163°-167° C. with decomposition. IR 3470, 3366, 1718, 1682 (m), 1656, 1608 (m), 1586 (m), 1567 (m), 1274, 1268, 718 $cm^{-1}$; MS (CI) 448 (100%, M+1), 326 (35%, M+1-PhCOOH); $^1H$ NMR ($CDC_{13}$) δ 0.82 (3H, s, $C_{18}$-Me , 1.07 (s, $C_{19}$-Me), 1.15 (d, $C_{22}$-Me), 3.71 (2H, v br, $NH_2$), 4.07 (1H, dd, ½ $C_{21}$-$CH_2$, 4.35 (1H, dd, ½ $C_{21}$-$CH_2$), 5.98 (1H dd), 6.30 (1H dd), 7.35 (2H, t), 7.57 (1H, t), 8.04 (2H, dd).

EXAMPLE 12

If the procedures as described in Examples 1 to 4 are repeated using the appropriate starting materials, the following compounds are obtained:

4-Amino-17β-hydroxymethylandrost-4-en-3-one.
4-Amino-17β-hydroxymethylandrosta-4,6-dien-3-one.
(20S)-4-Amino-20-hydroxypregn-4-en-3-one.
(20S)-4-Amino-20-hydroxypregna-4,6-dien-3-one.
(20R)-4-Amino-20-hydroxypregn-4-en-3-one.
(20R)-4-Amino-20-hydroxypregna-4,6-dien-3-one.
(20S)-4-Amino-20-hydroxypregna-4,16-dien-3-one.
(20S)-4-Amino-20-hydroxypregna-4,6,16-trien-3-one.
(20R)-4-Amino-20-hydroxypregna-4,16-dien-3-one.
(20R)-4-Amino-20-hydroxypregna-4,6,16-trien-3-one.
(20S)-4-Amino-20,21-dihydroxypregn-4-en-3-one.
(20R)-4-Amino-20,21-dihydroxypregna-4,6-dien-3-one.
4-Amino-21-hydroxypregn-4-en-3-one.
4-Amino-21-hydroxypregna-4,6-dien-3-one.
(20S)-4-Amino-21-methoxy-20-methylpregn-4-en-3-one.
(20R)-4-Amino-21-methoxy-20-methylpregn-4-en-3-one.
(20S)-4-Amino-21-methoxy-20-methylpregna-4,6-dien-3-one.
(20S)-4-Amino-21-(phenylmethoxy)-20-methylpregn-4-en-3-one.

(20R)-4-Amino-21-(phenylmethoxy)-20-methylpregn-4-en-3-one.

(20S)-4-Amino-21-(phenylmethoxy)-20-methylpregna-4,6-dien-3-one.

(20S)-4-Amino-21-[(4-chlorophenyl)methoxy]-20-methylpregn-4-en-3-one.

(20S)-4-Amino-21-[(4-methylphenyl)methoxy]-20-methylpregn-4-en-3-one.

(20S)-4-Amino-21-ethoxy-20-methylpregn-4-en-3-one.

(20S)-4-Amino-21-(2-phenylethoxy)-20-methylpregn-4-en-3-one.

What is claimed is:

1. A method for inhibiting $C_{17-20}$ lyase enzyme which comprises administering, to a patient in need of such inhibition, an effective amount of a compound of the formula:

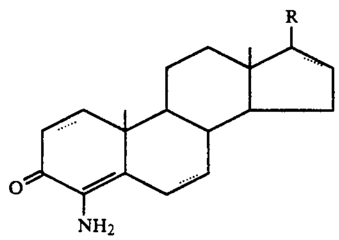

wherein the dotted lines indicate the optional presence of a double bond, R is —($C_{1-6}$ alkyl)-OZ Or —($C_{2-6}$-alkyl)-$(OZ)_2$ and Z is hydrogen, $C_{1-6}$ alkyl, phenyl—($C_{1-4}$ alkyl), (Y-substituted phenyl)—($C_{1-4}$ alkyl), $C_{1-6}$ alkanoyl, benzoyl or Y-substituted benzoyl wherein Y is methyl, halogen or methoxy.

2. A method according to claim 1 for inhibiting $C_{17-20}$ lyase enzyme wherein the compound administered is (20S)-4-amino-21-hydroxy-20-methylpregn-4-en-3-one.

3. A method according to claim 1 for inhibiting $C_{17-20}$ lyase enzyme wherein the compound administered is (20S)-4-amino-21-hydroxy-20-methylpregna-4,6-dien-3-one.

4. A method for treating androgen-dependent disorders by inhibiting $C_{17-20}$ lyase which comprises administering, to a patient in need of such treatment, an effective lyase-inhibiting amount of a compound of the formula:

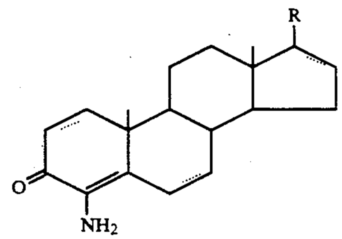

wherein the dotted lines indicate the optional presence of a double bond, R is —$C_{1-6}$ alkyl)-OZ Or —($C_{2-6}$ alkyl)-$(OZ)_2$ and Z is hydrogen, $C_{1-6}$ alkyl, phenyl—($C_{1-4}$ alkyl), (Y-substituted phenyl)—($C_{1-4}$ alkyl), $C_{1-6}$ alkanoyl, benzoyl or Y-substituted benzoyl wherein Y is methyl, halogen or methoxy.

5. A method according to claim 4 for treating androgen-dependent disorders wherein the compound administered is (20S)-4-amino-21-hydroxy-20-methylpregn-4-en-3-one.

6. A method according to claim 4 for treating androgen-dependent disorders wherein the compound administered is (20S)-4-amino-21-hydroxy-20-methylpregna-4,6-dien-3-one.

7. A method for treating benign prostatic hypertrophy by inhibiting $C_{17-20}$ lyase which comprises administering, to a patient in need of such treatment, an effective amount of a compound of the formula:

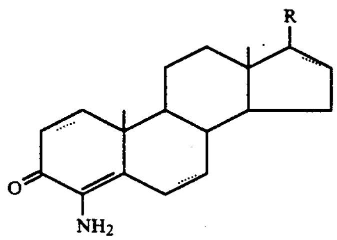

wherein the dotted lines indicate the optional presence of a double bond, R is —($C_{1-6}$ alkyl)-OZ or —($C_{2-\delta}$ alkyl)-$(OZ)z$ and Z is hydrogen, $C_{1-6}$ alkyl, phenyl—($C_{1-4}$ alkyl), (Y-substituted phenyl)—($C_{1-4}$ alkyl), $C_{1-6}$ alkanoyl, benzoyl or Y-substituted benzoyl wherein Y is methyl, halogen or methoxy.

8. A method according to claim 7 for treating benign prostatic hypertrophy wherein the compound administered is (20S)-4-amino-21-hydroxy-20-methylpregn-4-en-3-one.

9. A method according to claim 7 for treating benign prostatic hypertrophy wherein the compound administered is (20S)-4-amino-21-hydroxy-20-methylpregna-4,6-dien-3-one.

* * * * *

UNITED STATES PATENT AND TRADEMARK OFFICE

CERTIFICATE OF CORRECTION

PATENT NO. : 5,143,909

DATED : September 01, 1992

INVENTOR(S) : Philip M. Weintraub, et al

It is certified that error appears in the above-indentified patent and that said Letters Patent is hereby corrected as shown below:

Column 2, line 46 reads "IC5s", should read -- $IC_{50}$ --.
Column 2, line 64 reads "38", should read -- 3β--.
Column 6, line 53 reads "-4- -one", should read -- -4-en-3-one --.
Column 8, line 28 reads "β5β-", should read -- β,5β- --.
Column 9, line 58 reads "($CDC_{13}$)", should read -- ($CDC1_3$) --.
Column 9, line 64 reads "methylprehnan" should read -- methylpregnan --.
Column 10, line 36 reads "($CDC_{13}$)", should read -- ($CDC1_3$) --.
Column 10, line 37 reads "$CH_{2}$,", should read -- $CH_2$), --.
Column 11, line 35 reads "Or", should read -- or --.
Column 12, line 42 & 43 reads "$C_{2-t}$alkyl)-$(OZ)_z$", should read -- $C_{2-6}$ alkyl)-$(OZ)_2$ --.

Signed and Sealed this

Fourteenth Day of December, 1993

Attest:

BRUCE LEHMAN

Attesting Officer

Commissioner of Patents and Trademarks